United States Patent [19]

Fifolt

[11] 4,361,521
[45] Nov. 30, 1982

[54] DIFLUOROPHTHALOYL FLUORIDE

[75] Inventor: Michael J. Fifolt, Grand Island, N.Y.

[73] Assignee: Occidental Chemical Corporation, Niagara Falls, N.Y.

[21] Appl. No.: 228,656

[22] Filed: Jan. 26, 1981

[51] Int. Cl.³ ............................................. C07C 63/22
[52] U.S. Cl. ................................................ 260/544 F
[58] Field of Search ................................... 260/544 F

[56] References Cited

FOREIGN PATENT DOCUMENTS 154856 of 1963 U.S.S.R. ........................... 260/544 F

OTHER PUBLICATIONS

Odinokov, V. N. et al., *Chemical Abstracts*, vol. 69, (1968), #18,797z, plus p. #34,187S of the 8th cummulative index.

*Primary Examiner*—Natalie Trousof
*Assistant Examiner*—L. Hendriksen
*Attorney, Agent, or Firm*—J. F. Tao; A. S. Cookfair

[57] ABSTRACT

A novel fluorinated aromatic compound, 4,5-difluorophthaloyl fluoride, is prepared by reacting 4,5-dichlorophthalic anhydride with a stoichiometric excess of potassium fluoride.

1 Claim, No Drawings

DIFLUOROPHTHALOYL FLUORIDE

BACKGROUND OF THE INVENTION

This invention relates to a fluorinated compound, 4,5-difluorophthaloyl fluoride, and to a method for the preparation thereof. 4,5-Difluorophthaloyl fluoride is useful as a chemical intermediate in the preparation of various chemical end products, such as 4,5-difluorophthalimide and resins such as polyamides, and the like. Polyamides having fluorine substituents on the polymer chain may be prepared by polycondensation of 4,5-difluorophthaloyl fluoride with a suitable diamine, such as piperazine, utilizing such known techniques as interfacial polymerization or solution polymerization.

SUMMARY OF THE INVENTION

In accordance with this invention 4,5-difluorophthaloyl fluoride is prepared by reacting 4,5-dichlorophthalic anhydride with anhydrous potassium fluoride. The temperature of the reaction may vary considerably for example, from about 150° or lower to 300° Celsius or higher. The reaction is preferably carried out in the presence of a catalyst, at a temperature in the range of about 190° to about 280° Celsius.

The preferred catalysts that may be employed in the fluorination step are polyether catalysts, such as crown ethers, polyethylene glycols, or alkoxy polyethylene glycols, such polyethers typically having a molecular weight ranging from about 200 to about 25,000. Typically, the catalysts are employed in amounts of about 0.1 to about 20 percent, and preferably about 5.0 to about 15 percent by weight, based on the amount of chlorophthalic anhydride.

The fluorination reaction is preferably and conveniently carried out under atmospheric pressure conditions. However super-atmospheric and subatmospheric conditions may be employed, if desired.

Although it is preferred to run the fluorination reaction neat, an inert solvent, such as a dipolar aprotic solvent may be employed if desired. Suitable solvents include, for example, dimethylsulfoxide; dimethylformamide; N-methyl-2-pyrrolidinone; sulfolane; hexamethylphosphoramide, and the like.

The proportion of reactants may vary widely from a stoichiometric proportion to substantial molar excess of the fluoride reactant. Typically a molar ratio of potassium fluoride:dichlorophthalic anhydride of about 4:1 to about 20:1 is employed. Higher ratios may be employed but are not necessary and are generally less economical.

The following specific example is provided to further illustrate this invention and the manner in which it may be carried out. It will be understood, however, that the specific details given have been chosen for purpose of illustration and are not to be construed as a limitation on the invention. In the example, unless otherwise indicated, all parts and percentages are by weight and all temperatures are in degrees Celsius.

EXAMPLE 1

A reaction mixture was prepared by mixing and grinding together, 21.7 parts of 4,5-dichlorophthalic anhydride and 58 parts of anhydrous potassium fluoride. The mixture was charged to a reaction vessel together with 2 parts of Carbowax ® MPEG 200 catalyst, heated to about 210° C. and maintained thereat for about 6.5 hours. The mixture was then cooled to about 25° C. and allowed to stand for about 16 hours, then reheated and maintained at about 210° for 7.5 hours. The reaction product was purified by vacuum distillation to yield 2.43 parts of product. Analysis of the product by $C^{13}$ nuclear magnetic resonance and infra-red analysis confirmed it to be 4,5-difluorophthaloyl fluoride.

What is claimed is:

1. 4,5-difluorophthaloyl fluoride.

* * * * *